United States Patent [19]

Perez

[11] 4,456,461
[45] Jun. 26, 1984

[54] SEPARATION OF LOW BOILING CONSTITUENTS FROM A MIXED GAS

[75] Inventor: Ethelwolbo P. Perez, London, England

[73] Assignee: Phillips Petroleum Company, Bartlesville, Okla.

[21] Appl. No.: 416,204

[22] Filed: Sep. 9, 1982

[51] Int. Cl.³ .............................................. F25J 3/02
[52] U.S. Cl. ......................................... 62/28; 62/30; 62/31; 62/34; 62/39
[58] Field of Search .................. 62/18, 23, 24, 28, 26, 62/29, 33, 34, 31, 38, 30; 55/27, 48, 55, 68, 73

[56] References Cited

U.S. PATENT DOCUMENTS 4,322,225 3/1982 Bellinger et al. ....................... 55/48

Primary Examiner—Frank Sever

[57] ABSTRACT

Lower boiling constituents are separated from a normally gaseous feed mixture predominating in higher boiling constituents and containing significant amounts of such lower boiling constituents and having a first pressure substantially above atmospheric pressure and a first temperature substantially below atmospheric temperature and at which first pressure and first temperature, said feed mixture includes both vapor and liquid phases, including introducing at least a portion of the vapor of the feed mixture representing a second vapor phase into a separation contacting zone adjacent the top thereof at a second pressure substantially lower than the first pressure and a second temperature substantially lower than the first temperature and introducing at least a portion of the liquid of the feed mixture representing a second liquid phase into the separation-contacting zone at a lower intermediate point at a third pressure and a third temperature approximately equal to the first pressure and the first temperature, respectively. The second pressure thus being substantially lower than the third pressure and the second temperature thus being substantially lower than the third temperature, separating the second vapor phase and the second liquid phase in the separation-contacting zone to produce a third vapor phase substantially enriched in the higher boiling constituents and a third liquid phase substantially enriched in the lower boiling constituents, introducing the third vapor phase into a fractional distillation zone adjacent the top thereof and introducing the third liquid phase into the fractional distillation zone at an upper intermediate point, fractionally distilling the third vapor phase and the third liquid phase to produce a fourth vapor phase substantially enriched in the higher boiling constituents and a fourth liquid phase substantially enriched in lower boiling constituents, recovering the fourth vapor phase as a product and recovering the fourth liquid phase as a product. In accordance with another aspect, at least a portion of the second vapor phase and/or at least a portion of the third vapor phase is expanded in a turbo expander.

28 Claims, 1 Drawing Figure

SEPARATION OF LOW BOILING CONSTITUENTS FROM A MIXED GAS

The present invention relates to the separation of lower boiling constituents from a normally gaseous feed mixture predominating in higher boiling constituents and containing significant amounts of said lower boiling constituents. A more specific aspect of the present invention relates to a method of separating ethane and higher molecular weight hydrocarbons from a natural gas feed mixture predominating in methane and containing significant amounts of said ethane and high molecular weight hydrocarbons.

BACKGROUND OF THE INVENTION

The problems associated with prior art systems for separating higher and lower boiling constituents or a mixture thereof is best illustrated by the separation of natural gas. Natural gas, as it is received from a subsurface formation, generally is not suitable for use directly, without some processing. The initial processing operations carried out in a natural gas plant are to first remove acid gases, such as $CO_2$ and $H_2S$ and then pass the gas through a dehydration system to remove water. Thus, it would be advantageous if one of these preliminary treatment steps, such as the removal of $CO_2$ could be eliminated while still producing acceptable products. The resulting product can then be used as a fuel. However, such natural gases generally contain significant amounts of higher molecular weight hydrocarbons, such as ethane and to a lesser extent, propane, butanes and higher molecular weight hydrocarbons. The ethane and higher molecular weight hydrocarbons contribute relatively little heating value to the natural gas and have a significantly greater value as chemical feedstocks than as a fuel. Therefore, it is also highly advantageous to maximize the recovery of ethane and higher molecular weight hydrocarbons.

The natural gas feed to a natural gas plant will generally be at about atmospheric temperature and at an elevated pressure substantially above atmospheric pressure, either as received from the producing formation or having been compressed. Therefore, it has long been known to separate ethane and higher molecular weight hydrocarbons from methane by a combination of plural cooling stages and an expansion stage and separate the cooled and expanded fluid in a demethanizer to produce a vapor stream substantially enriched in methane content and a liquid stream substantially enriched in ethane and higher molecular weight hydrocarbons. However, such systems are not particularly efficient. Accordingly, it has been proposed in the past to improve the efficiency by utilizing two or more expansion stages in series. Even with such multiple expansion stages in a series, separation is still rather inefficient and difficult. First, the demethanizer either must be rather large and/or a given size demethanizer is limited in its throughput capacity. Secondly, the amounts of ethane retained in the separated methane stream is generally higher than desirable. The heat required by the demethanizer is rather high, thus, reducing the energy efficiency of the plant. The energy generated by the expanders is usually inadequate to handle all of the pressure requirements and the refrigeration needs of the overall plant. Finally, if $CO_2$ is not removed from the gas by prior treatment, amounts of $CO_2$ in the ethane and higher molecular weight hydrocarbon fraction are higher than desirable.

SUMMARY OF THE INVENTION

It is therefore an object of the present invention to overcome the above-mentioned and other problems and disadvantages of the prior art. Another object of the present invention is to provide an improved method for separating lower boiling constituents from a gaseous feed mixture predominating at higher boiling constituents and containing significant amounts of such lower boiling constituents. Yet another object of the present invention is to provide an improved method for separating ethane and higher molecular weight hydrocarbons from a natural gas containing predominant amounts of methane and significant amounts of such ethane and higher molecular weight hydrocarbons. Another and further object of the present invention is to provide an improved method for separating lower boiling constituents from a normally gaseous feed mixture predominating in higher boiling constituents and containing significant amounts of such lower boiling constituents by cryogenic means. Yet another object of the present invention is to provide an improved method for separating lower boiling constituents from a normally gaseous feed mixture predominating in higher boiling constituents and containing significant amounts of such lower boiling constituents by a combination of cryogenic and expansion means. Still another object of the present invention is to provide an improved method for separating lower boiling constituents from a normally gaseous feed mixture predominating in higher boiling constituents and containing significant amounts of such lower boiling constituents involving a novel separating-contacting step. A further object of the present invention is to provide an improved method for separating lower boiling constituents from a normally gaseous feed mixture predominating higher boiling constituents and containing significant amounts of said lower boiling constituents by a novel separation-contacting step preceded by an expansion step and/or followed by another expansion step. A still further object of the present invention is to provide an improved method for separating lower boiling constituents from a normally gaseous feed mixture predominating in higher boiling constituents and containing significant amounts of such lower boiling constituents involving a novel separation-contacting step followed by fractional distillation. Another and further object of the present invention is to provide an improved method in accordance with the next previous object wherein the size of the fractional distillation unit may be reduced and/or the throughput of a given size fractional distillation unit may be increased. A still further object of the present invention is to provide an improved method in accordance with the next two previous objects wherein the heat required in a fractional distillation step may be significantly reduced. A further object of the present invention is to provide an improved method for separating lower boiling constituents from a normally gaseous feed mixture predominating in higher boiling constituents and containing significant amounts of such lower boiling constituents in which the removal of the lower boiling constituents is substantially improved. Still another object of the present invention is to provide an improved method for separating ethane and higher molecular weight hydrocarbons from a natural gas predominating in methane and containing significant amounts of such ethane and higher molecular weight hydrocarbons, as well as carbon dioxide, while reducing the carbon dioxide content of the ethane and higher molecular weight hydrocarbon product. Yet another object of the present invention is to provide an improved method for separating lower boiling constituents from a normally gaseous feed mixture predominating in higher boiling constituents and containing significant amounts of such lower boiling constituents which includes at least one expansion stage and in which the energy produced by the expansion is significantly increased. These and other objects and advantages of the present invention will be apparent from the following description.

In accordance with the present invention, a normally gaseous feed mixture predominating in higher boiling constituents and containing significant amounts of lower boiling constituents and having a first pressure substantially above atmospheric pressure and a first temperature substantially below atmospheric temperature and, at which pressure and temperature, the feed mixture comprises both vapor and liquid phases, including introducing at least a portion of the vapor phase of the feed mixture into a separation-contacting zone adjacent the top thereof at a second pressure substantially lower than the first pressure and a second temperature substantially lower than the first temperature and introducing at least a portion of the liquid phase of the feed mixture into the separation-contacting zone at a lower intermediate point at a third pressure and a third temperature approximately equal to the first pressure and the first temperature, respectively, said second pressure thus being substantially lower than said third pressure and said second temperature being substantially lower than said third temperature, separating the introduced vapors and liquids in the separation-contacting zone to produce a second vapor phase substantially enriched in higher boiling constituents and a second liquid phase substantially enriched in lower boiling constituents, introducing at least a portion of the vapor of the second vapor phase to a fractional distillation zone adjacent the top thereof, introducing the remaining portion, if any, of the second liquid phase to the fractional distillation zone at a lower intermediate point, fractionally distilling the thus introduced vapors and liquids to produce a third vapor phase substantially enriched in higher boiling constituents and a third liquid phase substantially enriched in lower boiling constituents, recovering the third vapor phase as a product and recovering the third liquid phase as a product. In another embodiment, the first vapor phase is expanded by passing the same through a turbo expander to produce the second pressure and the second temperature and the thus expanded first vapor phase is passed to the separation-contacting zone without further treatment and/or at least a portion of the vapor of the second vapor phase is expanded by passing the same through a turbo expander and passing the thus expanded fluid to the fractional distillation zone without further treatment.

BRIEF DESCRIPTION OF THE DRAWING

The single FIGURE of drawings is a schematic illustration of a natural gas plant which can be employed in the practice of one embodiment of the present invention.

DESCRIPTION OF THE PREFERRED EMBODIMENTS

Figure 1:
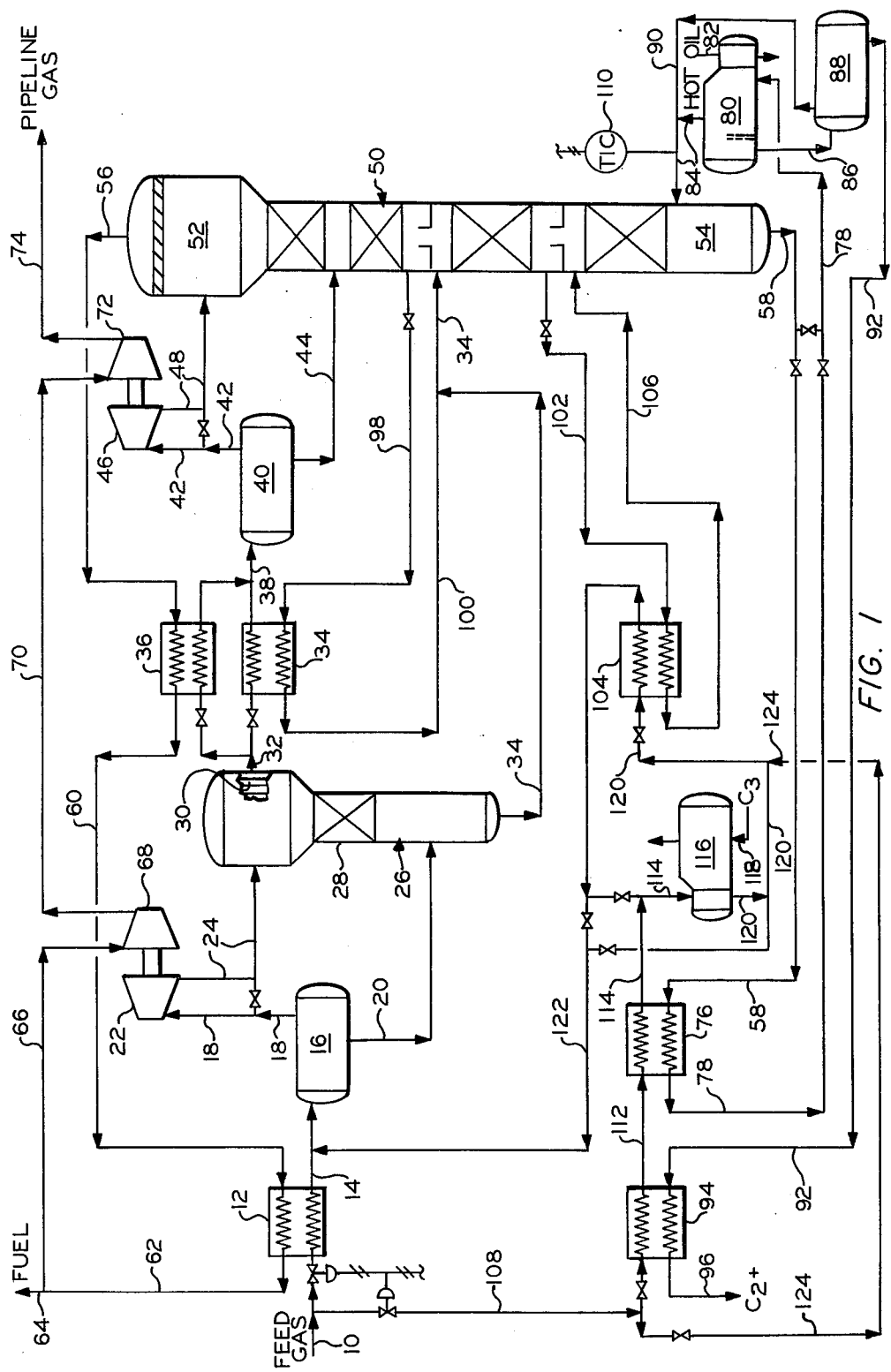

The method and apparatus of the present invention can best be illustrated by a description with reference to the drawing, which shows a preferred embodiment of the present invention utilizable in the separation of a natural gas feed.

In accordance with the drawing, a feed gas, such as natural gas, is introduced to the system through line 10. The feed gas will normally be at about atmospheric temperature and at an elevated pressure substantially above atmospheric pressure, for example, between about 300 and about 1100 psia. The natural gas feed will predominate in methane and contains significant amounts of ethane and higher molecular weight hydrocarbons in addition to small amounts of water, $CO_2$ and $H_2S$. For purposes of illustration, it is assumed that the $H_2S$ and water have been preliminarily removed from the feed gas. However, in accordance with one aspect of the present invention, the $CO_2$ has not been preliminarily removed.

The feed gas from line 10 is then cooled in heat exchanger 12 to reduce the temperature to a temperature substantially below atmospheric temperature in order to produce a fluid stream 14 comprising both vapor and liquid phases. Feed stream 14 is then introduced into a separator which is adapted to separate a vapor phase, which is discharged through line 18, and a liquid phase, which is discharged through line 20. The vapor phase is passed through a turbo expander 22 where the fluid is expanded to thereby substantially reduce the pressure and substantially reduce the temperature thus producing yet another fluid stream comprising both vapor and liquid phases, which is discharged through line 24. In order to provide flexibility, a part of the vapor phase through line 18 may bypass turbo expander 22. The fluid passing through line 24 is then introduced into a separator-contactor 26 adjacent the upper end thereof and the liquid phase passing through line 20 is introduced into separator contactor 26 at a lower intermediate point.

As indicated, the fluid passing through line 24 is at a substantially lower pressure and a substantially lower temperature than the original feed mixture and, consequently, also that of the liquid phase passing through line 20. Therefore, the fluid to the top of separator-contactor 26 has a substantially lower pressure and a substantially lower temperature than the feed to the bottom of separator-contactor 26. This substantial difference in the temperature and pressure of the fluids in separator-contactor 26 in and of itself results in substantially improved separation of vapors and liquids in the separator-contactor. However, still better results are obtained if the upper and lower portions of separator-contactor 26 are separated by an extended contact surface while they are countercurrently contacting one another. While the extended contact surface may be a plurality of tray-type contact surfaces, in a preferred embodiment the extended contact surface is a packing 28. The packing 28 in a specific example, will comprise one-inch metal pall rings. Also by way of example, the packing 28 would comprise about 10 to about 20% of the volume of separator-contactor 26. The packing material thus serves to reject some of the rising hot vapor and return it to the bottom of the separator-contactor and boil some of the descending cool liquid, thereby, converting a portion to vapors which are returned back to the upper portion of the contactor-separator. Still further improvement in separation of vapor from liquid in the separator-contactor 26 can be attained by providing separator veins 30 in the top of separator-contactor 26 to thereby restrict the flow of fluids in a cross-sectional direction and again improve separation. The difference in pressure between the top and the bottom of separator contactor 26 may, for example, be between about 150 and about 250 psia and the difference in temperature between the top and the bottom of the separator contactor may, for example, be between about 20° and about 40° F.

Separator-contactor 26 produces yet another vapor phase, which is discharged through line 32, and another liquid phase, which is discharged through line 34. The vapor phase in line 32 may be further cooled in order to condense a portion of the vapor phase and produce a fluid comprising both vapor and liquid phases by passing the same through indirect heat exchanger 34 and/or indirect heat exchanger 36. The thus cooled fluid is then passed through line 38 to a separator 40. Separator 40 separates the fluid into another vapor phase, which is discharged through line 42, and another liquid phase, which is discharged through line 44. The vapor phase passing through line 42 is then expanded by passing the same through turbo expander 46 to thereby substantially reduce the pressure and substantially reduce the temperature and provide a fluid stream comprising both vapor and liquid which is discharged through line 48. Fluids passing through line 48, line 44 and line 34 are introduced into a frictional distillation unit 50, which in the example being described as a demethanizer unit, at the top, an upper intermediate point and a lower intermediate point. Fractional distillation unit 50 may be any of such known fractional distillation units comprising multiple trays, multiple packed sections or a combination thereof. In the specific example being described, fractional distillation unit 50 comprises a plurality of packed sections and trap-out trays for purposes of withdrawing, heating and returning fluid to the column as hereinafter described. Fractional distillation unit 50 is also preferably made up of an upper rectifying section 52 and a lower stripping section 54. Fractional distillation unit 50 is heated, as hereinafter described. In fractional distillation unit 50, introduced fluids are further separated into a vapor phase, which is discharged through line 56, and a liquid phase, discharged through line 58. The vapor phase passing through line 56 will be substantially enriched in methane while the liquid phase through line 58 will predominate in ethane and higher molecular weight hydrocarbons. The vapor phase passing through line 56 may have the cooling energy thereof utilized to cool the entering feed gas. Specifically, the vapor phase passing through line 56 is passed in indirect heat exchange through heat exchanger 36 to thereby cool the vapor phase passing through line 32 then pass through line 60 and/or through heat exchanger 12 to thereby cool the feed gas introduced through line 10 and, finally, pass through line 62. Obviously, the methane or residue gas passing through line 62 will be at a low pressure. However, at this low pressure, it can still be utilized as an inplant fuel gas by withdrawing at least a portion thereof through line 64. If, however, the gas stream from line 62 is to be sold as a pipeline gas or otherwise transmitted to another location, the pressure thereof should be substantially increased. For this purpose, the residue gas is passed through line 66 to turbo compressor 68 which is driven by turbo expander 22, thence through line 70 and/or through turbo compressor 72 and, finally, through line 74. In order to heat fractional distillation unit 50, a portion of the liquid phase withdrawn through line 58 may be heated by passing the same through indirect heat exchanger 76, which is warmed by feed gases, hereinafter, described, and then passed through line 78. From line 78, the stream may be further heated by passing the same through demethanizer trim reboiler 80, which can be heated by an indirect heating medium, such as hot oil introduced through line 82. Vapors from reboiler 80 are discharged through line 84 to fractional distillation unit 50 at a point adjacent the bottom thereof. Liquids from reboiler 80 are discharged through line 86 to a surge tank 88 which separates vapors from liquids, combines the vapors passing through line 90 with the vapors passing through line 84 and returns the same to fractional distillation unit 50. Liquids separated in surge tank 88 are discharged through line 92, passed through heat exchanger 94 and recovered as a product through line 96. Heating of fractional distillation unit 50 can be additionally provided by withdrawing a sidestream from above a trap-out tray through line 98 to cool vapor phase passing through line 32 and thence returning the same to the fractional distillation unit through line 100, where it is combined with the liquid phase passing through line 34 and returned to the fractional distillation unit 50 below the trap-out tray. Similarly, a lower intermediate heating can be supplied to fractional distillation unit 50 by withdrawing a sidestream from a lower intermediate point through line 102, passing the same through heat exchanger 104, where it functions to cool a hereinafter mentioned portion of the feed mixture and is then returning the same through line 106 to a point below the trap-out tray from which it was withdrawn. Heating of fluids passing through heat exchangers 94, 76 and 104 can be provided by withdrawing a portion of the feed gas from line 10 through line 108. The volume of feed gas withdrawn through line 108 may be controlled, for example, by temperature indicator controller 110, mounted in line 84 of the trim reboiler system. Feed gas withdrawn through line 108 may then be passed through heat exchanger 94 in indirect heat exchange with the product, (ethane and higher hydrocarbons), thence through line 112, then through heat exchanger 76 where it warms the portion of $C_2$ and higher hydrocarbons utilized for heating the bottom of the fractional distillation column. From heat exchanger 76, the feed gas then flows through line 114 to propane chiller 116, which is supplied with propane as a refrigerant through line 118. After passing through chiller 116, the feed gas is discharged through line 120, thence through heat exchanger 104, where it heats the sidestream withdrawn from the fractional distillation column 50, and thence through line 122, where it is recycled back to the feed gas passing through line 14. Since the portion of the feed gas passing through heat exchangers 94, 76 and 104, has thus been cooled in its travels, it can be recycled back to the feed gas downstream of heat exchanger 12. As an alternative, all or part of the feed gas withdrawn through line 108 may be passed through line 124 directly to heat exchanger 104.

The following specific example further illustrates the method of the present invention.

A feed gas suitable for processing in accordance with the present invention would have a composition as listed in Table 1 below.

TABLE 1

| Component | Feed Gas Mol % | Residue Gas Mol % | NGL Mol % |
|---|---|---|---|
| $CO_2$ | 0.64 | 0.36 | 1.67 |

TABLE 1-continued

| Component | Feed Gas Mol % | Residue Gas Mol % | NGL Mol % |
|---|---|---|---|
| $N_2$ | 1.10 | 1.40 | 0.0 |
| $H_2S$ | Nil | Nil | Nil |
| $C_1$ | 76.63 | 96.87 | 0.10 |
| $C_2$ | 11.87 | 1.33 | 51.03 |
| $C_3+$ | 9.78 | Nil | 46.26 |

$C_2$ in NGL 91.20+
$C_3+$ in NGL 99.95+

A computer simulation of the processing of this feed gas, in accordance with the present invention and through the system as illustrated in the FIGURE, was carried out. Table 1, above, lists the composition of the residue gas passing through line 56 of the FIGURE and the natural gas liquids (NGL product) passing through line 86 of the FIGURE. The natural gas liquids product retained 91.20+% of the ethane originally present in the feed gas and 99.95+% of the $C_3+$ fraction originally present in the feed gas. Table 2 below illustrates typical temperatures and pressures of streams passing through selected lines of the FIGURE of the drawings.

TABLE 2

| Line No. | Temp of | Press. psia |
|---|---|---|
| 10 | 90 | 650 |
| 14 | −59 | 633 |
| 18 | −59 | 633 |
| 20 | −59 | 633 |
| 24 | −87 | 440 |
| 32 | −87 | 440 |
| 34 | −75 | 442 |
| 42 | −120 | 435 |
| 44 | −120 | 435 |
| 48 | −159.5 | 217 |
| 56 | −159.5 | 215 |
| 58 | 7.0 | 217 |
| 86 | 30.00 | 217 |

While specific materials, specific items of equipment, specific techniques and specific modes of operation have been set forth herein, it is to be understood that such specific recitals are by way of illustration and to set forth the best mode of operation in accordance with the present invention and are not to be considered limiting.

That which is claimed:

1. A method for separating ethane and higher molecular weight hydrocarbons from a natural gas feed, predominating in methane and containing significant amounts of said ethane and higher molecular weight hydrocarbons and having a first pressure substantially above atmospheric pressure and a first temperature substantially below atmospheric temperature, at which first pressure and first temperature, said feed comprises both a vapor phase, representing a first vapor phase, and a liquid phase, representing a first liquid phase, comprising:

(a) expanding at least a part of said vapor phase, in a first expansion step, to produce a first expanded fluid having a second pressure substantially lower than said first pressure and a second temperature substantially lower than said first temperature;

(b) introducing all of said first expanded fluid and any unexpanded first vapor phase into a separation-contacting zone adjacent the top thereof and introducing all of said first liquid phase into said separation-contacting zone at a lower intermediate point thereof, under conditions and in proportions such that the pressure at the top of said separation-contacting zone is substantially lower than the pressure at the bottom of said separation-contacting zone and the temperature at said top of said separation-contacting zone is substantially lower than the temperature at said bottom of said separation-contacting zone;

(c) separating said first expanded fluid, said unexpanded remaining portion of said first vapor phase and said first liquid phase, in said separation-contacting zone, to produce a second vapor phase and a second liquid phase;

(d) introducing said second vapor phase into a fractional distillation zone adjacent the top thereof and introducing said second liquid phase into said fractional distillation zone at an intermediate point thereof below the point of introduction of said second vapor phase;

(e) fractionally distilling said second vapor phase and said second liquid phase, in said frictional distillation zone, to produce a third vapor phase predominating in methane and containing insignificant amounts of ethane and higher molecular weight hydrocarbons and a third liquid phase predominating in ethane and higher molecular weight hydrocarbons and containing insignificant amounts of methane; p1 (f) recovering said third vapor phase as a product; and (g) recovering said third liquid phase as a product.

2. A method in accordance with claim 1 wherein the first vapor phase and the first liquid phase are produced by separating the feed, in a first separation zone.

3. A method in accordance with claim 2 wherein the feed having a first pressure substantially above atmospheric pressure and a first temperature substantially below atmospheric temperature is produced by cooling a natural gas having said first pressure and a temperature near atmospheric temperature, in a first cooling step.

4. A method in accordance with claim 3 wherein the third vapor phase is utilized to supply cooling, in the first cooling step, by passing said third vapor phase in indirect heat exchange with the feed.

5. A method in accordance with claim 1 wherein the second vapor phase is cooled, in a second cooling step, prior to introduction into the fractional distillation zone.

6. A method in accordance with claim 5 wherein the second vapor phase is thus cooled, in the second cooling step, by indirect heat exchange with at least one of (1) the third vapor phase and (2) a first side stream withdrawn from an upper intermediate point in said fractional distillation zone.

7. A method in accordance with claim 6 wherein the first side stream is withdrawn from the fractional distillation zone at an upper intermediate point above the point of introduction of the second liquid phase, passed in indirect heat exchange with the second vapor phase and returned to said fractional distillation zone with the second liquid phase, to thereby at least partially heat said fractional distillation zone.

8. A method in accordance with claim 5 wherein the second vapor phase thus cooled, in the second cooling step, is separated, in a second separation step, to produce a fourth vapor phase and a fourth liquid phase.

9. A method in accordance with claim 8 wherein at least a part of the fourth vapor phase is expanded in a second expansion step, to produce a second expanded fluid and said second expanded fluid is introduced into the top of the fractional distillation zone and the fourth liquid phase is introduced into the fractional distillation zone between the point of introduction of said second expanded fluid and the point of introduction of the second liquid phase.

10. A method in accordance with claim 1 or 9 wherein the fractional distillation zone comprises an upper rectifying section and a lower stripping section, all vapor phases introduced into said fractional distillation zone are introduced into said rectification section and all liquid phases introduced into said fractional distillation zone are introduced into said stripping section.

11. A method in accordance with claim 1 or 9 wherein the fractional distillation zone is heated at least in part by withdrawing a second side stream from said fractional distillation zone at a lower intermediate point thereof, passing the same in indirect heat exchange with a part of the warmest available feed, in a first heating zone, and returning the thus heated second side stream to said fractional distillation zone at a point below its point of withdrawal.

12. A method in accordance with claim 1 or 9 wherein the fractional distillation zone and the third liquid phase are heated at least in part by passing the third liquid phase in indirect heat exchange with part of the warmest available feed, in a second heating zone, separating the thus heated third liquid phase into a fifth vapor phase and a fifth liquid phase, in a third separation zone, returning said fifth vapor phase to said fractional distillation zone above the point of withdrawal of said third liquid phase, recovering said fifth liquid phase as the product predominating in ethane and higher molecular weight hydrocarbons and containing insignificant amounts of methane, and returning said portion of said feed thus utilized to supply heat to said fractional distillation zone to the main feed stream at a point at which the temperature of said main feed stream is approximately equal to the temperature of the thus returned portion of the feed.

13. A method in accordance with claim 12 wherein the volume of the part of the feed thus utilized to supply heat to the fractional distillation zone is controlled in accordance with the temperature at which the thus heated fifth vapor phase is returned to said fractional distillation zone.

14. A method in accordance with claim 12 wherein the fifth liquid phase is passed in indirect heat exchange with the part of the feed utilized to supply heat to the fractional distillation zone, in a third heating step, prior to thus passing said part of the feed in indirect heat exchange with the third liquid phase, in the second heating step.

15. A method in accordance with claim 12 wherein the thus heated third liquid phase is further heated, in a fourth heating step, by an external source of heat and separated into a sixth vapor phase and a sixth liquid phase, the sixth vapor phase is returned to the fractional distillation zone and the sixth liquid phase is separated, in the third separation zone to produce the fifth vapor phase and the fifth liquid phase.

16. A method in accordance with claim 15 wherein the volume of the part of the feed thus utilized to supply heat to the fractional distillation unit is controlled in accordance with the temperature at which the thus warmed sixth vapor phase and the fifth vapor phase are returned to said fractional distillation zone.

17. A method in accordance with claim 1 or 9 wherein the fractional distillation zone is heated at least in part by passing a part of the warmest available feed in indirect heat exchange with a second side stream, withdrawn from said fractional distillation zone at a lower intermediate point and returned to said fractional distillation zone at a point below its point of withdrawal, in a first heating zone, with the third liquid phase, in a second heating zone, and with a fifth liquid phase, produced by separating the thus warmed third liquid phase into a fifth vapor phase and a fifth liquid phase, in a third heating step, the fifth vapor phase is returned to said fractional distillation zone at a point above the point of withdrawal of said third liquid phase, the fifth liquid phase is recovered as the product predominating in ethane and higher molecular weight hydrocarbons and containing insignificant amounts of methane, said part of said feed is returned to the main feed stream at a point at which the temperature of said main feed stream is approximately equal to the temperature of the thus returned portion of the feed, and said part of said feed is passed sequentially through said third heating step, said second heating step and said first heating step.

18. A method in accordance with claim 17 wherein the portion of the feed thus utilized to supply heat to the fractional distillation zone is cooled, with an external cooling medium, in a third cooling step, between the first heating step and the second heating step.

19. A method in accordance with claim 35 wherein the volume of the portion of the feed thus utilized to supply heat to the fractional distillation zone is controlled in accordance with the temperature at which the fifth vapor phase is returned to said fractional distillation zone.

20. A method in accordance with claim 17 wherein the thus heated third liquid phase is further heated, in a fourth heating step, by an external source of heat, and separated into a sixth vapor phase and a sixth liquid phase, the sixth vapor phase is returned to the fractional distillation zone and the sixth liquid phase is separated, in the third separation zone, to produce the fifth vapor phase and the fifth liquid phase.

21. A method in accordance with claim 20 wherein the volume of the portion of the feed thus utilized to supply heat to the fractional distillation zone is controlled in accordance with the temperature at with the fifth vapor phase and the sixth vapor phase are returned to the fractional distillation zone.

22. A method in accordance with claim 1 or 9 wherein the feed also contains significant amounts of carbon dioxide and the third liquid phase contains substantially reduced amounts of said carbon dioxide.

23. A method in accordance with claim 1 or 9 wherein the feed also contains significant amounts of nitrogen and the third vapor phase contains a major portion of said nitrogen.

24. A method in accordance with claim 1 or 9 wherein the first expansion step and the first and second expansion step, as the case may be, are performed in expansion sections of turbo expander-compressors in which said extension sections drive compressor sections.

25. A method in accordance with claim 24 wherein the third vapor phase is compressed in at least one of the compression sections of the turbo expander-compressors prior to recovery of said third vapor phase as a product.

26. A method in accordance with claim 1 or 9 wherein the second pressure is between about 150 and 250 psia below the first pressure and second temperature is between about 20° F. and about 40° F. lower than the first temperature.

27. A method in accordance with claim 1 or 9 wherein the separation-contacting zone has an extended contact surface located between the top and the bottom thereof and improved contact between rising vapors and descending liquids in said separation-contacting zone is obtained by passing said rising vapors and said descending liquids through said extended contact surface.

28. A method in accordance with claim 1 or 9 wherein the upper portion of the separation-contacting zone into which the first vapor phase is introduced has cross sectional flow restricting surfaces disposed therein and improved contact of vapors and liquids in said upper portion of said separation-contacting zone is obtained by passing said first expanded fluid and rising vapors in said separation-contacting zone through said cross sectional flow restricting surfaces.

* * * * *

UNITED STATES PATENT AND TRADEMARK OFFICE
CERTIFICATE OF CORRECTION

PATENT NO. : 4,456,461

DATED : June 26, 1984

INVENTOR(S) : Ethelwoldo P. Perez, London, England

It is certified that error appears in the above-identified patent and that said Letters Patent are hereby corrected as shown below:

Claim 1, Col. 7, Line 59, insert after "said" and before "vapor", ---first---. Col. 8, line 21, change "frictional" to ---fractional---. Col. 8, line 28, delete "p1".

Signed and Sealed this

Eleventh Day of June 1985

[SEAL]

Attest:

DONALD J. QUIGG

Attesting Officer  Acting Commissioner of Patents and Trademarks